United States Patent [19]

Moore

[11] Patent Number: 5,373,964
[45] Date of Patent: Dec. 20, 1994

[54] EYEDROP DISPENSER WITH FOCUSING LIQUID LENS

[76] Inventor: Sidney D. Moore, 2173 N. Wilkes Ct., Claremont, Calif. 91711

[21] Appl. No.: 81,680

[22] Filed: Jun. 23, 1993

[51] Int. Cl.⁵ ............................................. B65D 47/18
[52] U.S. Cl. ............................................ 222/1; 222/215; 222/420; 222/421; 604/295; 604/300
[58] Field of Search ............... 222/421, 215, 420, 566, 222/575, 1; 604/294, 295, 298, 300; 239/499, 500, 590.5

[56] References Cited

U.S. PATENT DOCUMENTS

| | | | |
|---|---|---|---|
| 2,736,316 | 2/1956 | Stovall | 604/300 |
| 2,987,223 | 6/1961 | Armour | 222/420 X |
| 3,979,117 | 9/1976 | Worsham | 273/102 B |
| 4,257,417 | 3/1981 | Gibilisco | 128/233 |
| 4,408,699 | 10/1983 | Stock | 222/149 |
| 4,550,866 | 11/1985 | Moore | 222/420 |
| 4,629,456 | 12/1986 | Edwards | 604/294 X |
| 4,773,551 | 9/1988 | Rizzardi | 222/420 X |
| 5,219,101 | 6/1993 | Matkovich et al. | 222/420 X |
| 5,221,017 | 6/1993 | Cistone et al. | 222/420 X |
| 5,246,145 | 9/1993 | Leoncavallo et al. | 222/420 X |

FOREIGN PATENT DOCUMENTS

| | | | |
|---|---|---|---|
| 0362911 | 4/1990 | European Pat. Off. | 222/420 |
| 814703 | 12/1936 | France | 222/420 |
| 358249 | 9/1922 | Germany | 222/420 |
| 1063755 | 10/1954 | Germany | 222/420 |
| 1318462 | 5/1973 | United Kingdom | 222/40 |
| 2053840 | 2/1981 | United Kingdom | 604/294 |

*Primary Examiner*—Andres Kashnikow
*Assistant Examiner*—Anthoula Pomrening
*Attorney, Agent, or Firm*—Christie, Parker & Hale

[57] ABSTRACT

An eyedrop dispenser uses the natural optical lens effect of a transparent droplet formed at the tip of the dispenser to focus the image of a target disposed inside the outlet of the dispenser. The target image is viewable by the user to align the droplet with the eye when dispensing eyedrops or other liquid medication. The target image is arranged so it comes into focus just prior to when the droplet being formed at the tip of the dispenser is ready to be released from the dispenser tip. The target image is formed by an image plane indicator device located inside the dispenser on the image plane of the droplet when the user is viewing the indicator through the natural transparent lens formed by the droplet. The indicator can be a pinhole through which the liquid contents pass prior to dispensing. The pinhole is focused by the lens and formed as a magnified image by the lens effect of the droplet. Other target-forming indicators can be positioned at or near the image plane to form enlarged optical images of targets useful for the accurate dispensing of the liquid contents.

24 Claims, 2 Drawing Sheets

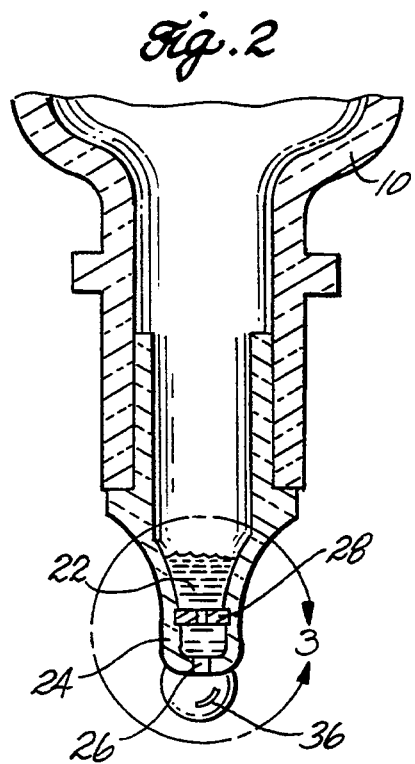
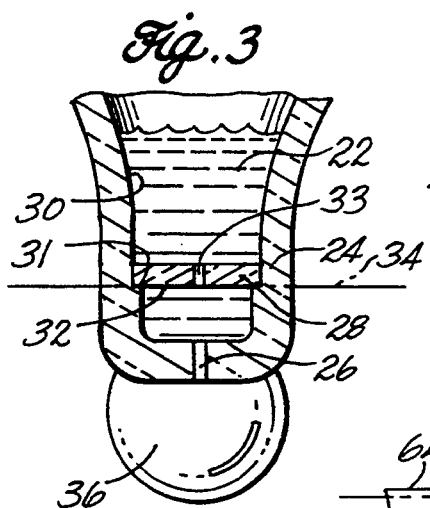
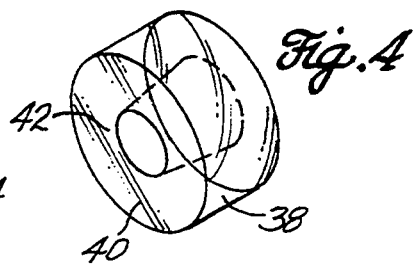
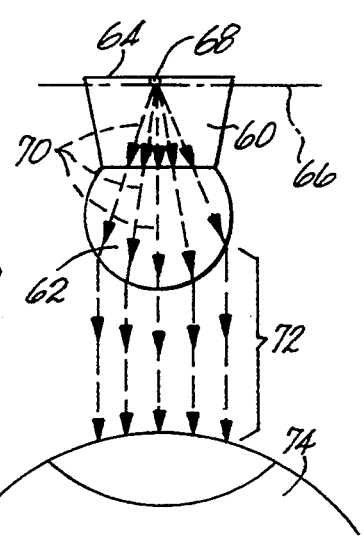
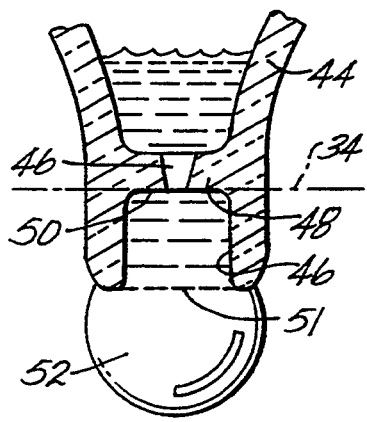

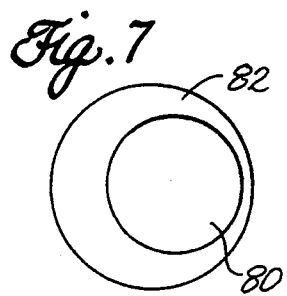
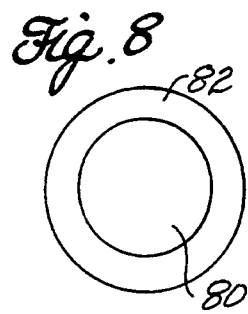
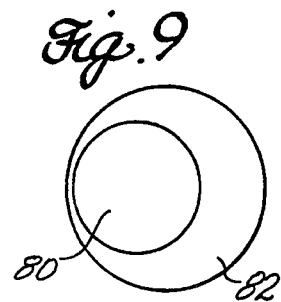
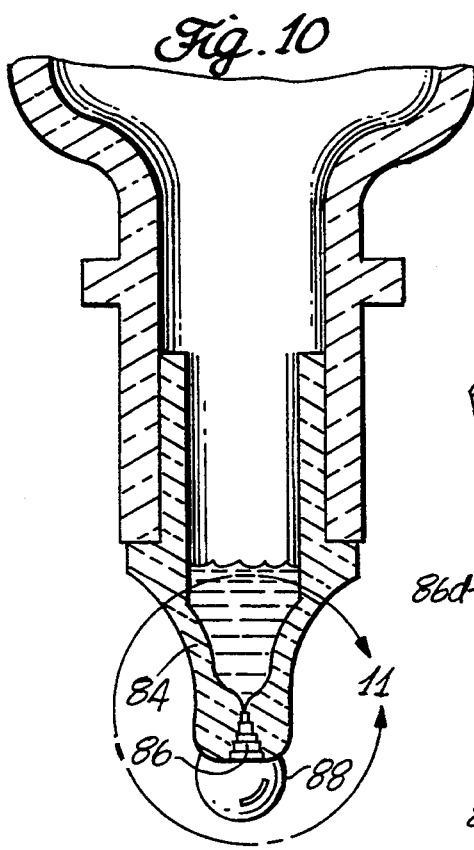
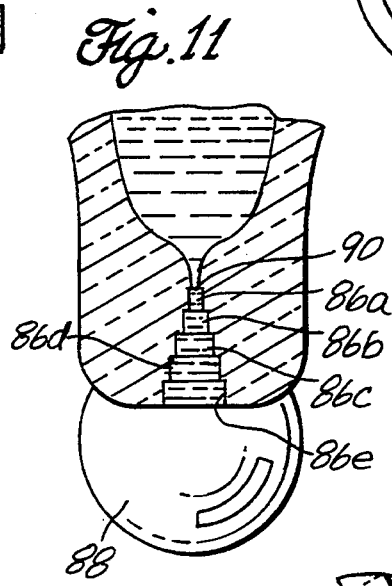
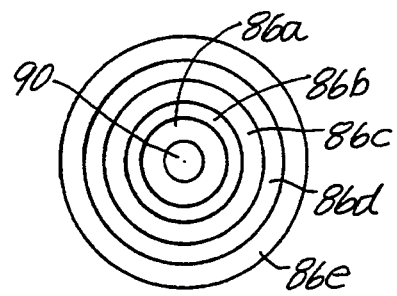
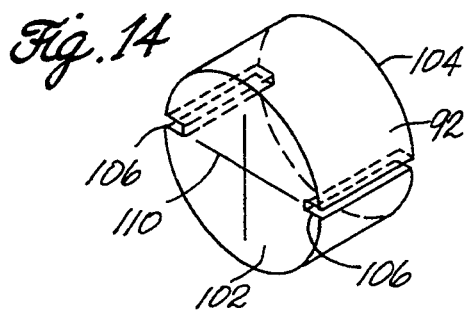
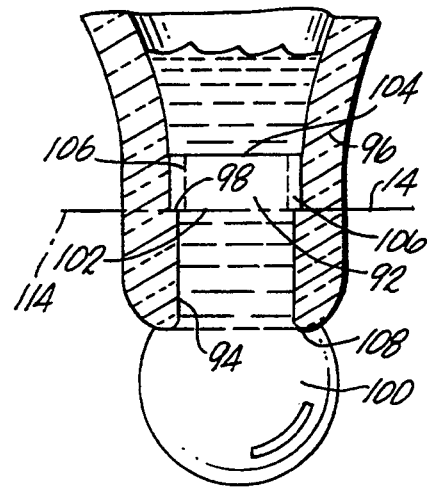

EYEDROP DISPENSER WITH FOCUSING LIQUID LENS

FIELD OF THE INVENTION

This invention relates to dispensers for eyedrops and liquid medications administered to the eye. More particularly, the invention provides a dispenser that enables the user to focus on an optical image of a target for accurately aligning the dispenser with the eye.

BACKGROUND OF THE INVENTION

Eyedrops and medications administered to the corneal surface of the eye are commonly dispensed from the familiar plastic squeeze bottle. The wall of the container is deformable inwardly to force the liquid medication through the open end of a nozzle-like dispensing tip in the well-known manner.

There are a number of now-familiar problems in using these eyedrop dispensers. For instance, it is difficult for the user to hold the dispenser tip steady while holding the eye open and the head tilted back in a steady position so the tip of the dispenser does not contact the eye. It is important to dispense the medication near the center of the eye; improper alignment can result in little if any medication reaching the eye. However, dispensers of the prior art must be held well inside the close focusing limit of the eye which is six to eight inches. Thus, it is not possible to view the tip of the dispenser at the critical position for dispensing drops onto the corneal surface.

There are instances in which medication administered to the eye must be carefully measured drop-by-drop for proper dosage prescribed by a physician. As an example, medications for the heart and other vital organs may be administered through eyedrops. Therefore, it is desirable, and often critical, to dispense medications to the eye with drop-by-drop accuracy.

Prior art devices intended to improve administration of eyedrop solutions to the eye have resulted in questionable improvements over the simple squeeze bottle that is still used for virtually all eyedrop solution containers. One modified dispenser of the prior art is disclosed in U.S. Pat. No. 4,550,866 to Moore (no relation). This patent discloses a dispensing device in which the nozzle has been modified to provide a multicolored target to aid the user in accurately focusing on the nozzle to position it relative to the eye when the medication is dispensed.

U.S. Pat. No. 4,257,417 to Gibilisco discloses a bottle holder having a nose rest and a bar with an opening through which the tip of the dispenser is mounted to slidably position and hold the dispenser over the eye.

Another prior art eyedrop dispenser sold under the name "Suredrop" includes a cup-shaped eyedrop guide that removably connects to the end of the dispenser. A special plug is unscrewed from the dispenser tip before use. Use of this device leads to contact between the user's fingers and the inside of the eye cup. Directions require thorough washing and sterilization with each use.

The minimal advantages of these prior art devices have not been sufficient to justify the additional manufacturing expense as well as effort and cost to the user. The simple squeeze bottle type dispenser continues to be the choice of virtually all eye care solution manufacturers.

The present invention avoids the disadvantages inherent in the prior art dispensers, while providing a novel close-focus capability for accurate visual positioning of the dispensing tip over the eye. As will be described in more detail below, the invention is used to controllably form a droplet of the liquid solution at the dispenser tip so that the user may visually observe the exact moment when the droplet will be released. This close-focus dispenser also enables the user to accurately align the droplet with the center of the eye. The present invention, as a result, eliminates significant negative factors associated with .use of prior eyedrop dispensers. These disadvantages include: (1) as previously emphasized, the inability of the human eye to focus upon an object as close as the dispensing tip must be for effective use, and (2) anticipation of the subsequent shock experienced by the user when the released drop, surprisingly strikes the sensitive corneal surface of the eye. The latter effect produces the familiar involuntary flinch response and squeamish feeling of anticipation that users commonly experience, which frustrates the process of administering eyedrop solutions comfortably and effectively.

The foregoing deficiencies of the prior art are overcome by the present invention which enables the user to visually observe and carefully control progressive development and release of the droplet, while also enabling precise optical alignment of the dispensing tip over the center of the cornea for accurate administration of the solution.

In addition, the present invention may be readily adapted to existing production equipment at very little expense. Only slightest modification of existing dispenser molding equipment is required. No changes are required to the basic geometry of the nozzle or dispensing tip components, nor to other components of the otherwise conventional plastic squeeze bottle dispenser. This avoids use of more expensive and bulky external dispenser guides and the resulting sanitation problems that may be associated with their use.

SUMMARY OF THE INVENTION

This invention provides an eyedrop dispenser which uses the natural optical lens effect of a droplet formed at the tip of the dispenser to focus the optical image of a target disposed inside the outlet of the dispenser. The target image is viewable by the user to align the droplet with the center of the eye when dispensing eyedrops or other liquid solutions. The target is arranged on a focal plane member inside the dispenser so that the image of the target comes into focus when the droplet being formed at the tip of the dispenser is ready to be released from the dispenser tip. The target is positioned on the image plane of the droplet when the user visually observes the target through the natural transparent lens formed by the droplet. The focal plane member can comprise a pinhole through the center of a disk aligned on the image plane. The solution passes through the pinhole prior to dispensing of the liquid in droplet form. The pinhole can provide the target, the image of which is magnified by the lens formed by the droplet. This forms a greatly enlarged target image visible to the user through the naturally transparent lens formed by the droplet. Ambient light entering the container and passing through the transparent solution highlights the pinhole as a well-defined magnified image that forms the target. The disk can be of a color different from the target, which improves the contrast necessary to enhance the user's ability to see and focus upon the target image. Other target-forming indicators can be positioned at or near the image plane of the droplet to form enlarged optical images of various targets used for the accurate dispensing of the liquid contents.

In one embodiment of the invention, a single target plane is formed at the image plane of the droplet formed on the dispenser tip. In another embodiment, a multiple image plane device is located inside the dispensing tip to provide multiple progressive magnified target images that focus in sequence as the droplet is progressively formed at the dispensing tip. These multiple targets come into and out of focus in a progressive pattern that can be used for alignment of the droplet over the center of the eye while also precisely indicating to the user the exact moment when the droplet will be released.

Thus, the invention provides a magnified viewable image of the droplet's formation and development at the dispenser tip, to enable the user to visually control with extreme accuracy the aim and number of drops administered.

These and other aspects of the invention will be more fully understood by referring to the following detailed description and the accompanying drawings.

BRIEF DESCRIPTION OF THE DRAWINGS

FIG. 1 is an elevational view illustrating one embodiment of an eyedrop dispenser according to principles of this invention.

FIG. 2 is a fragmentary cross-sectional view illustrating another embodiment of a focusing dispensing tip of a dispenser.

FIG. 3 is an enlarged fragmentary view taken within the circle 3 of FIG. 2.

FIG. 4 is a perspective view illustrating an alternative target-forming device used in a focusing dispenser tip.

FIG. 5 is an alternative embodiment of the focusing dispenser tip shown in FIGS. 2 and 3.

FIG. 6 is a schematic view showing the lens effect of a droplet formed at the tip of the dispenser.

FIGS. 7, 8 and 9 are schematic views illustrating target images that are decentered to the left, centered, and decentered to the right, respectively.

FIG. 10 is a fragmentary cross-sectional view of an alternative embodiment of a focusing dispenser tip which provides multiple progressively focused images.

FIG. 11 is an enlarged fragmentary cross-sectional view taken within the circle 11 of FIG. 10.

FIG. 12 is a schematic view illustrating a target image formed by the focusing dispenser tip of FIGS. 10 and 11.

FIG. 13 is a fragmentary cross-sectional view illustrating a further alternative embodiment of a focusing dispenser tip.

FIG. 14 is a perspective view illustrating the target-forming device of FIG. 13.

DETAILED DESCRIPTION

FIGS. 1 through 3 show an eyedrop dispenser 10 which comprises a clear plastic squeeze bottle having a hollow interior for containing a liquid eyedrop solution. The walls of the container are transparent or translucent so that ambient light can enter the interior of the container. The liquid eyedrop solution also is transparent or translucent so that light entering the interior of the container can be visible through the liquid. (The container and the liquid will be referred to herein as transparent, but this term will be understood to also mean translucent for simplicity of description.)

The dispenser 10 includes a dispensing tip having a nozzle-shaped end portion 12. A narrow internal passage 14 of circular cross-section is centered in the nozzle and communicates with the liquid in the container. The passage 14 opens through the external end of the dispensing tip to form an outlet passage 16. A focal plane member 18 in the form of a thin disk traverses the passage 16. The disk rests on an annular shoulder inside the passage 14 through the nozzle. A pinhole centered in the disk is aligned with the center of the passage 14 through the nozzle. During use, when the walls of the squeeze bottle are deformed inwardly, liquid in the interior of the container is forced through the passage 14 and passes through the pinhole and out the dispensing tip formed by the narrow tube 16. A droplet of liquid is formed on the exterior tip of the tube. The natural lens effect of the transparent droplet is used to form a focused magnified target image which provides a means for accurately aligning the dispenser tip with the eye, as described below.

The invention provides a means for enabling dispensing of liquid solutions administered to the eye with drop-by-drop accuracy. Liquid solutions that can be used are transparent to the extent that the natural lens effect of the droplet can be used to focus ambient light on a target within the outlet of the dispenser. Liquid solutions that can be used are conventional over-the-counter eyedrops and medications available under a doctor's prescription.

FIGS. 2 and 3 are fragmentary cross-sectional views of the dispenser 20 which comprises a transparent plastic squeeze bottle containing a liquid eyedrop solution 22. This dispenser has an open end on which a dispensing nozzle 24 is mounted, The nozzle opens into the interior of the container and includes an outlet 26 aligned on the axis of symmetry of the nozzle. Referring to FIG. 3, a focal plane member 28 in the form of a thin circular disk is centered in a passageway 30 leading to the outlet 26. The disk 28 rests on an annular shoulder 31 formed within the interior passage of the nozzle. A pinhole 33 passes through the center of the disk. The pinhole axis is centered in a radial planar surface 32 of the disk 28 so that the pinhole 33 and disk 28 cooperate to form a viewable target (described below). The pinhole axis is concentrically aligned with the axis of the outlet 26. The pinhole diameter is smaller than the diameter of the outlet 26. The narrow diameter of the pinhole 33 controls the flow of liquid through the outlet 26 when the squeeze bottle is inverted and its walls deformed inwardly to form a droplet 36 at the tip of the dispenser. The outlet 26 at the exterior of the dispenser is oversized with respect to the diameter of the pinhole so the pinhole is visible through the oversized passage 26. The annular shoulder 31 is positioned on a focal plane (shown in phantom lines 34) of the droplet 36 formed at the exterior of the dispensing tip. This positions both the front face 32 of the disk 28 and the front opening of the pinhole 33 on the focal plane 34 of the droplet.

FIG. 4 is a perspective view showing an insert 38 that can provide an alternative focal plane member. The insert has a radial planar front face 40 and a tapered axial passage 42 of a diameter similar to the diameter of the pinhole 33. The insert 38 is sized to securely press-fit within the wall of the passage 30 when the insert 38 is inserted into the passage 30 during assembly. The insert 38 and other focal plane members described herein are preferably made from a transparent material having a color different from that of the container and the nozzle. Additionally, the nozzle and the container are preferably of the same transparent or translucent material. In use, the contrast provided by the difference in color visually distinguishes the radial target surface 40 from light passing through the axial passage 42 when viewing the target surface through the natural lens formed by the droplet.

FIG. 5 illustrates a cross-sectional view of a further alternative embodiment of the invention. In this embodiment, a dispensing tip 44 has a tapered axial bore 46 through an integral image plane member 48 which provides a radial target surface 50 facing an outlet 51. The front face of the tapered bore is aligned on the center of the target surface 50. The target may be of a contrasting color compared to the container and nozzle to increase the contrast between it and the image of the bore 46 formed by the lens effect of a droplet 52 formed on the end of the dispensing tip.

In using the dispenser, the user holds the dispenser in the usual inverted position over the corneal surface of the eye and presses the walls of the container inwardly by finger pressure to form a droplet on the exterior of the dispensing tip. The user can control the size of the droplet by increasing or decreasing finger pressure. The droplet shown in the drawings represents the proportionate size of a droplet formed just prior to its release from the tip of the dispenser. The user observes formation of the droplet by focusing his/her eye on the droplet. The droplet forms the equivalent of an optical plano-convex lens and produces a magnified image of the pinhole which is located at the image plane of focus of the lens-forming droplet. This magnified image forms a centering target observable by the user as the user looks through the lens-forming droplet. Since the front face of the disk is of a darker color than the pinhole, which in a sense admits white light, the target appears as a bright white dot in the middle of a preferably different colored target surface magnified greatly in size by the lens effect of the droplet. Moreover, as the droplet is being formed and its formation is observed by the user's eye, the magnified image of the target suddenly comes into focus when the droplet reaches a predetermined size that focuses light directly on the image plane of the droplet. This lens size is preferably the size of the droplet just prior to its release. A differently shaped droplet, say, a smaller droplet that is in the process of being formed, will not have its focal plane coincident with the focal plane of the target; and therefore, the droplet will continue to appear blurred to the user until the droplet is formed large enough to bring its focal plane into coincidence with the focal plane of the target and thereby instantly focus upon the target and produce a magnified image of the target. Continued finger pressure on the container then causes the droplet to be released at an instant fully under the control of the user.

In addition to producing a target image at the moment before the droplet is released, the dispenser tip is naturally centered over the eye when the observer's eye sees the magnified image of the target. Any deviation in centering can be easily detected by observing when the magnified target image has moved radially away from its centered position over the eye.

FIG. 6 illustrates the phenomenon involved in the focusing of a magnified image of a target through the natural lens effect of a droplet. This view schematically shows a dispenser tip 60, a droplet 62 of liquid solution on the tip of the dispenser, a target—forming disk 64 on an image plane 66 of the droplet 62, a pinhole 68 in the center of the disk 64, and focused light rays 70 passing through the transparent droplet 62 as collimated light in the region 72 passes toward the eye 74. The droplet 62 and the eye 74 each form the equivalents of opposed optical collimators. The bottom surface of the droplet has a curvature that forms the equivalent of a short focal length (close focus) lens. In one embodiment, the focal length is in the range of two to four millimeters. This produces large magnification of the small pinhole which is believed to be magnified in the range of sixty to eighty times the normal size of the pinhole. The target formed by the pinhole and the droplet act as a collimator of light passing to the eye. This guarantees alignment of the target image when the droplet is moved to a substantially centered position over the eye.

The present invention has the advantage that both nearsighted and farsighted persons can use the lens effect of the droplet to clearly focus on the target. The short focal length lens effect, with its corresponding long depth of field, naturally brings the image into sharp focus independently of whether the user is nearsighted or farsighted. With the prior art dispensers having no means of focal plane focus of a magnified target there is nothing in focus close to the eye and the user's vision of the dispenser tip appears blurred. In the present invention, the target and the droplet not only combine to form a classic collimator, which guarantees alignment when the user sees a centralized target, but it also ensures accurate drop delivery even when the target is misaligned. For instance, FIG. 7 is a schematic representation of a magnified image 80 of a pinhole in a disk 82 when the dispensing tip is decentered to the left over the axis of the eye. The magnified image of the pinhole 80 appears as a centered target in the disk when the dispenser tip is perfectly centered over the eye, as shown in FIG. 8, which is a schematic representation of the magnified image 80 of the pinhole centered FIG. 9 illustrates a magnified image of the pinhole when the dispensing tip is decentered to the right. In FIGS. 7 or 9, the dispenser tip is either moved by the user to the right or to the left, respectively, for centering the droplet over the eye.

FIGS. 10 through 12 illustrate an alternative form of the invention in which a dispenser nozzle 84 has a stepped outlet passage 86 that forms multiple magnified target images in sequence during formation of a droplet 88. In this embodiment, a narrow diameter opening 90 inside the dispenser opens into an entrance to the stepped passage 86. This narrow diameter opening is of essentially pinhole diameter in order to control the flow of solution that passes from the dispenser so as to control formation of the droplet 88. This narrow diameter opening opens into the multiple diameter passage 86 which includes plural sections 86a through 86e of progressively larger diameter. These multiple diameter sections form annular surface areas or rings with openings through them that are progressively larger when the stepped passage is viewed through the droplet 88. Each ring 88a–88e independently comes into sharp focus as the droplet is progressively formed at the tip of the dispenser. Each annular surface ring 88a–88e is located at a different image plane depending upon the size of the droplet as it forms. Thus, the user is able to observe the rings coming into sharp focus in sequence in a progression of larger diameter rings as the droplet becomes larger during its formation. When the largest ring appears in focus the droplet will be ready for release from the tip of the dispenser.

FIGS. 13 and 14 illustrate another alternative embodiment in which a focal plane member 92 is disposed in the center of a large cylindrical opening 94 at the base of a dispenser nozzle 96. The focal plane member 92 is in the form of a cylindrical insert which rests on an annular step 98 in the outlet passage of the dispenser nozzle. The step is on the focal plane of a droplet 100 formed on the tip of the dispenser and shown in FIG. 13 as phantom line 114. The insert 92 has a front face 102 and a cylindrical rear face 104. A pair of elongated narrow axial slots 106 extend through the front and rear end faces to communicate from the rear side to the front side of the insert. The slots provide passageways for the controlled transfer of eyedrop solution from the body of the container to the tip 108 at which the droplet 100 is formed. An indexing mark 110 preferably in the form of a thin cross-hair, with its axis of intersection at the center of the insert, provides a focal plane indicator centered on the axis of the passage 94. This focal plane indexing mark 110 is on the front face of the insert so as to be visible to the user who observes the indexing mark through the transparent droplet 100. Thus, a magnified optical image of the cross-hair is focusably viewable by the user for proper alignment of the solution container during the administration of the eyedrop solution.

The invention can be used in other dispensers without departing from the scope of the invention. This would include eye droppers with a substantially rigid tube having at one end a dispensing tip and having at its opposite end a squeezably deformable portion for controlling the formation of the droplet in response to a visible magnified target image formed on the focal plane of the droplet.

What is claimed is:

1. An eyedrop dispenser comprising:
   a deformable container having a hollow interior for containing a liquid solution dispensed from the container;
   a dispensing nozzle at the end of the container, the dispensing nozzle having a passageway through it for communication with the interior of the container for supplying liquid to an exterior tip of the dispensing nozzle in droplet form in response to inward pressure deforming the container;
   a focal plane member traversing the passageway through which the liquid passes prior to forming as a droplet of liquid on the exterior tip of the dispensing nozzle, the droplet having a focal plane, said focal plane member extending across the passageway on the focal plane of said droplet; and
   a target-forming indicator on the focal plane member, the focal plane member traversing the passageway sufficiently to form an area of focusability on said focal plane and on which said target-forming indicator is located, the target-forming indicator facing the dispensing nozzle and aligned with the droplet formed on the exterior tip of the dispensing nozzle so that the natural lens effect of the droplet focuses ambient light and thereby forms a magnified image of said target-forming indicator visible to a user visually observing the magnified image through the droplet.

2. Apparatus according to claim 1 in which the container is transparent or translucent.

3. Apparatus according to claim 2 in which the liquid solution is transparent or translucent.

4. Apparatus according to claim 1 in which the focal plane member is in a fixed position with the target-forming indicator located at the focal plane of the droplet substantially at the point of droplet formation when the droplet is ready to be released from the dispenser nozzle.

5. Apparatus according to claim 1 in which the focal plane member is a thin disk and the target-forming indicator is a pinhole which controls passage of liquid from the container to the passageway and which also provides the image of the target forming indicator that is magnified by the natural lens effect of the droplet.

6. Apparatus according to claim 5 in which the pinhole is centered on the axis of symmetry of the passageway.

7. Apparatus according to claim 1 in which the focal plane member comprises a plurality of said target-forming indicators that each sequentially form images of targets visually observable through the droplet.

8. Apparatus according to claim 7 in which the plurality of target-forming indicators is a series of displaced concentric steps.

9. Apparatus according to claim 1 in which a pinhole formed in the focal plane member offset from its axis of symmetry provides communication of the liquid solution from the container interior to the passageway for dispensing from the exterior tip of the dispensing nozzle, and in which the target-forming indicator is an indexing mark located at a point on the focal plane member aligned with the axis of symmetry of the passageway.

10. Apparatus according to claim 1 in which the liquid solution comprises medication for the eye.

11. Apparatus according to claim 1 in which the liquid solution comprises a medication for prescription use.

12. Apparatus according to claim 1 in which the focal plane member has a color different from that of the container.

13. Apparatus according to claim 1 in which the container is a plastic squeeze bottle with walls that are transparent to light.

14. Apparatus according to claim 13 in which the container includes a liquid solution that is transparent to light.

15. An eyedrop dispenser comprising a container for containing a liquid solution dispensed in droplet form from an exterior dispensing tip carried on the container, and focal plane image-forming means within an outlet portion of the dispenser positioned substantially on an image plane of a droplet so that the natural lens effect of the droplet focuses light and thereby produces a magnified image of a target on said focal plane visible to a user visually observing the target through the droplet.

16. Apparatus according to claim 15 in which the liquid solution comprises medication for the eye.

17. Apparatus according to claim 15 in which the liquid solution comprises a medication for prescription use administered to the eye.

18. Apparatus according to claim 15 in which the container comprises a plastic squeeze bottle having walls transparent to light and in which the liquid solution is transparent to light.

19. Apparatus according to claim 15 in which the container includes a substantially rigid tube having at one end the exterior dispensing tip and at the other end a squeezably deformable portion for controlling the formation of the droplet.

20. An eyedrop dispenser comprising:
   a container having a hollow interior containing a liquid solution for being dispensed from the container, the container having exterior walls which are plastically deformable and which transmit ambient light, the liquid solution being transparent to light;
   a dispensing nozzle at an end of the container and having a passageway through it with an outlet for supplying the liquid solution in the container to an exterior dispensing tip of the nozzle in droplet form in response to inward pressure deforming the container;
   a focal plane member traversing the passageway in the nozzle and through which the liquid solution passes prior to forming as a transparent droplet of liquid on an exterior portion of the dispensing tip, the droplet having a focal plane, the focal plane member having a visible surface aligned with the outlet substantially on the focal plane of the droplet; and
   a target indicator on the visible surface of the focal plane member, the focal plane member traversing the passageway sufficiently to form an area of focusability of said visible surface on said focal plane and on which said target indicator is located, said target indicator facing the dispensing tip and aligned with the droplet formed on the dispensing tip and being distinguishable from said visible surface so that the natural lens effect of the transparent droplet forms a short focal-length lens that focuses ambient light and thereby forms a magnified image of the target indicator on said focal plane member which is visible to a user visually observing the magnified image through the droplet.

21. Apparatus according to claim 20 in which the liquid solution comprises medication for the eye.

22. Apparatus according to claim 20 in which the liquid solution comprises a medication for prescription use administered to the eye.

23. A method of dispensing liquid medication to the eye, comprising:
   providing a container having a dispensing nozzle at one end and a passageway from the container through the nozzle to an external dispensing tip of the nozzle, in which the container is adapted for dispensing a succession of droplets from the tip of the nozzle,
   placing a focal plane member in the passageway on the focal plane of a droplet formed on the tip of the nozzle, the focal plane member having a focusable surface extending across the passageway with a target indicator thereon distinguishable from said focusable surface located on said focal plane and aligned with the passageway, and
   dispensing the liquid from the container into the eye of the user by the user's progressively forming a droplet on the tip of the dispensing nozzle while holding the dispensing tip sufficiently close to the eye so the user looks through the droplet and visually observes ambient light focused upon the target indicator producing a magnified image of the target indicator using the natural lens effect of the droplet, said magnified image coming into focus for the eye of the user at a precise time during formation of the droplet that indicates to the user that the droplet is about to be released from the dispensing tip.

24. A method of dispensing liquid medication to the eye, comprising:
   providing a container having a dispensing nozzle at one end and a passageway from the container through the nozzle to an external dispensing tip of the nozzle, in which the container is adapted for dispensing a succession of droplets from the tip of the nozzle,
   placing a focal plane member in the passageway on the focal plane of a droplet formed on the tip of the nozzle, the focal plane member having a focusable surface extending across the passageway with a target indicator thereon distinguishable from said focusable surface located on said focal plane and aligned with the passageway, and
   dispensing the liquid from the container into the eye of the user by the user's progressively forming a droplet on the tip of the dispensing nozzle while holding the dispensing tip sufficiently close to the eye so the user looks through the droplet and visually observes ambient light focused upon the target indicator producing a magnified image of the target indicator using the natural lens effect of the droplet, said magnified image providing a means for centering alignment of the dispensing tip over the eye of the user.

* * * * *